US 11,969,485 B2

United States Patent
Kelson et al.

(10) Patent No.: US 11,969,485 B2
(45) Date of Patent: Apr. 30, 2024

(54) CONTROLLED RELEASE OF RADIONUCLIDES

(71) Applicant: ALPHA TAU MEDICAL LTD., Tel Aviv (IL)

(72) Inventors: Itzhak Kelson, Tel Aviv (IL); Yona Keisari, Ramat Gan (IL); Michael Schmidt, Kfar Saba (IL); Amnon Gat, Matan (IL); Ofer Magen, Hod Hasharon (IL); Guy Keret, Beit Yehoshua (IL); Amitai Sosnovitch, Nokdim (IL); Avia Berkowitz, Modiin (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 305 days.

(21) Appl. No.: 16/979,543

(22) PCT Filed: Mar. 28, 2019

(86) PCT No.: PCT/IB2019/052524
§ 371 (c)(1),
(2) Date: Sep. 10, 2020

(87) PCT Pub. No.: WO2019/193464
PCT Pub. Date: Oct. 10, 2019

(65) Prior Publication Data
US 2021/0008233 A1 Jan. 14, 2021

Related U.S. Application Data

(60) Provisional application No. 62/651,274, filed on Apr. 2, 2018.

(51) Int. Cl.
*A61K 51/12* (2006.01)
*A61K 9/00* (2006.01)
*A61N 5/10* (2006.01)

(52) U.S. Cl.
CPC ........ *A61K 51/1282* (2013.01); *A61N 5/1001* (2013.01); *A61K 9/0004* (2013.01); *A61K 9/0009* (2013.01); *A61K 9/0024* (2013.01)

(58) Field of Classification Search
CPC .. A61K 51/1282; A61K 51/02; A61K 9/0004; A61K 9/0009; A61K 9/0024;
(Continued)

(56) References Cited

U.S. PATENT DOCUMENTS 3,754,999 A 8/1973 Merges
3,811,426 A 5/1974 Culver et al.
(Continued)

FOREIGN PATENT DOCUMENTS

CN 101259290 A 9/2008
CN 101437467 A 5/2009
(Continued)

OTHER PUBLICATIONS

De Kruijff, R., Wolterbeek, H., Denkova, A. (2015). A critical review of alpha radionuclide therapy—how to deal with Recoiling Daughters? Pharmaceuticals, 8(2), 321-336. https://doi.org/10.3390/ph8020321 (Year: 2015).*
(Continued)

*Primary Examiner* — Christine H Matthews
*Assistant Examiner* — Marc D. Honrath
(74) *Attorney, Agent, or Firm* — KLIGER & ASSOCIATES PATENT ATTORNEYS LTD.

(57) ABSTRACT

A brachytherapy device including a base adapted for being at least partially introduced into a body of a subject and a plurality of radionuclide atoms of a first alpha-emitting isotope, coupled to the base in a manner that not more than 15% of the radionuclide atoms leave the base in 24 hours, in methods other than radioactive decay. When installed in a human subject, the brachytherapy device emits radionuclide
(Continued)

atoms of the first alpha-emitting isotope at a rate of at least 0.1% of the number of radionuclide atoms of the first alpha-emitting isotope coupled to the base, per 24 hours.

49 Claims, 1 Drawing Sheet

(58) Field of Classification Search
CPC .... A61K 47/34; A61N 5/1001; A61N 5/1007; A61N 2005/1024; A61N 2005/101; A61P 35/00
See application file for complete search history.

(56) References Cited

U.S. PATENT DOCUMENTS

| | | | |
|---|---|---|---|
| 4,107,283 A | 8/1978 | Pratt et al. | |
| 4,652,459 A | 3/1987 | Engelhardt | |
| 4,697,575 A * | 10/1987 | Horowitz | A61N 5/1001 600/8 |
| 4,976,680 A | 12/1990 | Hayman et al. | |
| 5,342,283 A | 8/1994 | Good | |
| 5,531,662 A * | 7/1996 | Carr | A61N 5/1014 607/101 |
| 5,713,828 A | 2/1998 | Coniglione | |
| 5,716,317 A | 2/1998 | Okano et al. | |
| 6,030,333 A | 2/2000 | Sioshansi et al. | |
| 6,059,714 A | 5/2000 | Armini et al. | |
| 6,060,036 A | 5/2000 | Armini | |
| 6,077,413 A | 6/2000 | Haefeli et al. | |
| 6,099,458 A | 8/2000 | Robertson | |
| 6,224,536 B1 | 5/2001 | Pike | |
| 6,248,057 B1 * | 6/2001 | Mavity | A61N 5/1027 600/3 |
| 6,254,552 B1 * | 7/2001 | Lewis | A61K 51/1282 600/3 |
| 6,352,682 B2 * | 3/2002 | Leavitt | A61K 51/06 424/1.29 |
| 6,391,911 B1 | 5/2002 | Bases | |
| 6,392,068 B1 | 5/2002 | Lu et al. | |
| 6,394,945 B1 | 5/2002 | Chan et al. | |
| 6,475,644 B1 | 11/2002 | Hampikian et al. | |
| 6,575,888 B2 | 6/2003 | Zamora et al. | |
| 6,589,502 B1 | 7/2003 | Coniglione et al. | |
| 6,635,234 B1 | 10/2003 | Arsen et al. | |
| 6,638,205 B1 | 10/2003 | Chan et al. | |
| 6,666,811 B1 | 12/2003 | Good | |
| 6,676,595 B1 | 1/2004 | Delfino | |
| 6,709,693 B1 | 3/2004 | Dinkelborg et al. | |
| 6,716,156 B2 | 4/2004 | Menuhr et al. | |
| 6,723,052 B2 | 4/2004 | Mills | |
| 8,821,364 B2 | 9/2014 | Fisher et al. | |
| 8,834,837 B2 * | 9/2014 | Kelson | A61N 5/1027 424/1.69 |
| 8,894,969 B2 | 11/2014 | Kelson et al. | |
| 9,539,346 B1 | 1/2017 | Larsen et al. | |
| 10,166,403 B2 | 1/2019 | Bakker et al. | |
| 2001/0005930 A1 | 7/2001 | Coniglione | |
| 2001/0006616 A1 | 7/2001 | Leavitt | |
| 2002/0055666 A1 | 5/2002 | Hunter et al. | |
| 2002/0055667 A1 | 5/2002 | Mavity et al. | |
| 2002/0077520 A1 | 6/2002 | Segal et al. | |
| 2002/0131935 A1 | 9/2002 | Fisher et al. | |
| 2003/0092957 A1 | 5/2003 | Scott et al. | |
| 2003/0118649 A1 * | 6/2003 | Gao | A61K 9/0024 424/471 |
| 2004/0018968 A1 | 1/2004 | Sgouros et al. | |
| 2004/0076579 A1 * | 4/2004 | Coniglione | A61K 51/1282 600/1 |
| 2004/0208821 A1 | 10/2004 | Larsen et al. | |
| 2004/0242953 A1 | 12/2004 | Good | |
| 2005/0159809 A1 * | 7/2005 | Hezi-Yamit | A61L 31/16 623/1.42 |
| 2005/0222013 A1 | 10/2005 | Jung et al. | |
| 2006/0014938 A1 | 1/2006 | Groman et al. | |
| 2006/0039858 A1 | 2/2006 | Dadachova et al. | |
| 2006/0142853 A1 | 6/2006 | Wang et al. | |
| 2006/0224035 A1 | 10/2006 | Russell, Jr. et al. | |
| 2006/0269475 A1 * | 11/2006 | Ryu | A61K 9/0097 424/1.11 |
| 2007/0041900 A1 * | 2/2007 | Kelson | A61K 51/1282 600/1 |
| 2008/0193374 A1 | 8/2008 | Arsen et al. | |
| 2008/0249398 A1 * | 10/2008 | Harder | A61N 5/1027 600/8 |
| 2009/0136422 A1 * | 5/2009 | Kelson | A61P 35/00 424/1.73 |
| 2009/0311173 A1 | 12/2009 | Kelson et al. | |
| 2009/0311413 A1 | 12/2009 | Kelson et al. | |
| 2010/0015042 A1 | 1/2010 | Keisari et al. | |
| 2010/0056844 A1 * | 3/2010 | Fisher | A61K 51/1251 600/8 |
| 2010/0062143 A1 | 3/2010 | Kelson et al. | |
| 2012/0123189 A1 | 5/2012 | Ribbing et al. | |
| 2013/0253255 A1 | 9/2013 | Van Niekerk | |
| 2014/0296612 A1 | 10/2014 | Schwartz | |
| 2015/0104560 A1 | 4/2015 | Kelson et al. | |
| 2015/0292061 A1 | 10/2015 | Fassbender et al. | |
| 2016/0250360 A1 | 1/2016 | Larsen | |
| 2017/0000911 A1 | 1/2017 | Larsen et al. | |
| 2017/0319871 A1 | 11/2017 | Pitman | |
| 2018/0345038 A1 | 12/2018 | Kelson et al. | |
| 2019/0022410 A1 | 1/2019 | Hermann et al. | |

FOREIGN PATENT DOCUMENTS

| | | | |
|---|---|---|---|
| EP | 1191121 A1 | 3/2002 | |
| EP | 1232769 A1 | 8/2002 | |
| RU | 2089143 C1 | 9/1997 | |
| RU | 2182022 C1 | 5/2002 | |
| RU | 2606108 C2 | 1/2017 | |
| WO | 9719706 A1 | 6/1997 | |
| WO | 9719724 A1 | 6/1997 | |
| WO | 9733628 A1 | 9/1997 | |
| WO | 9902194 A1 | 1/1999 | |
| WO | 9917812 A1 | 4/1999 | |
| WO | 9921615 A1 | 5/1999 | |
| WO | 0006243 A2 | 2/2000 | |
| WO | 0040275 A2 | 7/2000 | |
| WO | 0071204 A1 | 11/2000 | |
| WO | 0160417 A2 | 8/2001 | |
| WO | 0205859 A2 | 1/2002 | |
| WO | 00241923 A1 | 5/2002 | |
| WO | 02068000 A2 | 9/2002 | |
| WO | 2004026111 A2 | 4/2004 | |
| WO | 2004045549 A2 | 6/2004 | |
| WO | 2004096293 A2 | 11/2004 | |
| WO | 2006003123 A2 | 1/2006 | |
| WO | 2006043083 A2 | 4/2006 | |
| WO | 2006110889 A2 | 10/2006 | |
| WO | 2007013060 A1 | 2/2007 | |
| WO | 2007013060 A2 | 2/2007 | |
| WO | 2011018792 A1 | 2/2011 | |
| WO | 2015142316 A1 | 9/2015 | |
| WO | WO-2016205652 A1 * | 12/2016 | A61K 31/10 |
| WO | 2018207105 A1 | 11/2018 | |

OTHER PUBLICATIONS

De Kruijff, R., Wolterbeek, H., & Denkova, A. (2015). A critical review of alpha radionuclide therapy—how to deal with Recoiling Daughters? Pharmaceuticals, 8(2), 321-336. https://doi.org/10.3390/ph8020321 (Year: 2015).*

CN Application # 2019800233036 Office Action dated Jan. 12, 2022.

U.S. Appl. No. 16/610,507 Office Action dated Mar. 29, 2022.

Perry et al., "A method for testing the diffusion coefficient of polymer films", 1996 AARST International Radon Symposium, pp. 1-9, Sep. 29-Oct. 2, 1996.

(56) References Cited

OTHER PUBLICATIONS

Meyer et al., "Inhibition of neointimal proliferation with 188Re-labeled self-expanding nitinol stent in a sheep model", Radiology, vol. 229, issue 3, pp. 847-854, Dec. 2003.
Cooks et al., "Local Control of Lung Derived Tumors by Diffusing Alpha-Emitting Atoms Released From Intratumoral Wires Loaded With Radium-224", International Journal of Radiation Oncology*Biology*Physics, vol. 74, Issue 3, pp. 966-973, Jul. 1, 2009.
Arazi et al., "Treatment of solid tumors by interstitial release of recoiling short-lived alpha emitters", Physics in Medicine Biology ,vol. 52, Issue 16, pp. 5025-5042, Aug. 1, 2007.
Cooks et al., "Growth retardation and destruction of experimental squamous cell carcinoma by interstitial radioactive wires releasing diffusing alpha-emitting atoms", International Journal of Cancer, vol. 122, issue 7, pp. 1657-1664, Apr. 1, 2008.
Cooks et al., "Interstitial wires releasing diffusing alpha emitters combined with chemotherapy improved local tumor control and survival in squamous cell carcinoma-bearing mice", Cancer, vol. 115, issue 8, pp. 1791-1801, Apr. 15, 2009.
Thomson et al., "Stereotactic Multiple Are Radiotherapy", British Journal of Radiology, vol. 63, issue 754, pp. 745-751, 1990.
Orre et al., "Hyperfine interaction studies of radon in some metals and metal oxides with the alpha-gamma angular correlation method", Uppsala University, Institute of Physics, pp. 1-89, Nov. 1975.
Wood., "Displacement current and multiple pulse effects in plasma source ion implantation", Journal of Applied Physics, vol. 73, issue 10, pp. 4770-4778, May 15, 1993.
Free Dictionary "Embed", The Free Dictionary, 1 page, 2012.
Kirby et al., "The Radiochemistry of Radium", National Academy of Sciences, National Research Council, Nuclear Science Series, U.S Atomic Energy Commission, pp. 1-213, Dec. 1964.
Milkey, R., "Stability of Dilute Solutions of Uranium, Lead, and Thorium Ions", Analytical Biochemistry, vol. 26, pp. 1800-1803, 1954.
Stajnkrycer et al., "Chemical and Radiological Toxicity of Depleted Uranium", Military Medicine, vol. 169, Issue 3, pp. 212-216, Mar. 2004.
Tepe et al., "Prophylaxis of Restenosis With 186Re-Labeled Stents in a Rabbit Model", Circulation, vol. 104, pp. 480-485, year 2001.
Abildskov et al., "Hyperfine interactions of 220RN and 224RA implanted into Fe, Al, Cd and Bi metals", Nuclear Physics, issue A194, pp. 292-304, year 1972.
Dillman et al., "A Randomized Trial of Induction Chemotherapy plus High-Dose Radiation versus Radiation Alone in Stage III Non-Small-Cell Lung Cancer", The New England Journal of Medicine, vol. 323, issue 14, pp. 940-945, Oct. 4, 1990.
Le Chevalier et al., "Radiotherapy alone versus combined chemotherapy and radiotherapy in nonresectable non-small-cell lung cancer: first analysis of a randomized trial in 353 patients", Journal of National Cancer Institute, vol. 33, No. 6, pp. 417-423, Mar. 20, 1991.
Al-Sarraf et al., "Concurrent radiotherapy and chemotherapy with cisplatin in inoperable squamous cell carcinoma of the head and neck", An RTOG Study, Cancer, vol. 59, issue 2, pp. 259-265, Jan. 15, 1987.
O'Connell et al., "Improving adjuvant therapy for rectal cancer by combining protracted-infusion fluorouracil with radiation therapy after curative surgery", The New England Journal of Medicine, vol. 331, issue 8, pp. 502-507, Aug. 25, 1994.
Wolff et al., "Phase I trial of gemcitabine combined with radiation for the treatment of locally advanced pancreatic adenocarcinoma", Clinical Cancer Research, vol. 7, issue 8, pp. 2246-2253, Aug. 7, 2001.
Popovtzer et al., "Alpha-Particle Based Brachytherapy Treatment of Patients with Squamous Cell Carcinoma, a New Effective Concept", vol. 17, Issue 4, Supplement, p. S43, Aug. 31, 2018.
Wikipedia, "Radium", pp. 1-11, Mar. 5, 2017.
International Application PCT/IB2019/052524 Search Report dated Jul. 29, 2019.
CN application # 2018800298271 Office Action dated Jun. 4, 2021.
Arazi et al., "The Treatment of Solid Tumors by Alpha Emitters Released from (224)Ra-loaded Sources—Internal Dosimetry Analysis," Physics in Medicine and Biology, vol. 55, pp. 1203-1218, year 2010.
JP Application # 2019557389 Office Action dated Oct. 26, 2021.
IN Application # 202047044711 Office Action dated Dec. 6, 2021.
Arazi, "Diffusing Alpha-Emitters Radiation Therapy: Theoretical and Experimental Dosimetry," Ph.D. Thesis, Raymond and Beverly Sackler Faculty of Exact Sciences, School of Physics and Astronomy, Tel Aviv University, pp. 1-285, Sep. 2008.
CN Application # 2018800298271 Office Action dated Nov. 26, 2021.
EP Application # 19781797 Search Report dated Dec. 13, 2021.
EP Application # 18797701.2 Search Report dated Dec. 15, 2020.
CN Application # 2018800298271 Office Action dated Mar. 30, 2022.
International Application # PCT/IB2021/061687 Search Report dated Apr. 10, 2022.
JP Application # 2019557389 Office Action dated May 24, 2022.
RU Application # 2020130217 Office Action dated Jun. 3, 2022.
SG Application # 11201910176P Office Action dated Apr. 1, 2021.
AU Application # 2019247818 Office Action dated May 13, 2021.
JP Application # 2020-551517 Office Action dated Nov. 30, 2022.
SG Application # 11201910176P Office Action dated Aug. 1, 2022.
ARIPO Application # AP/P/2019011968 Office Action dated Sep. 8, 2022.
ARIPO Application # AP/P/2020012678 Office Action dated Sep. 12, 2022.
CN Application # 2019800233036 Office Action dated Sep. 20, 2022.
JP Application # 2020551517 Office Action dated Aug. 16, 2023.
CN Application # 2019800233036 Office Action dated Oct. 10, 2023.
U.S. Appl. No. 17/549,929 Office Action dated Aug. 24, 2023.
CN Application Office Action dated Apr. 28, 2023.
KR Application # 1020207030889 Office Action dated Nov. 23, 2023.
JP Application # 2023017195 Office Action dated Dec. 5, 2023.
EP Application # 19781797.6 Office Action dated Jan. 25, 2024.
IN Application # 202047044711 Hearing Notice dated Jan. 25, 2024.
U.S. Appl. No. 17/948,280 Office Action dated Dec. 19, 2023.

* cited by examiner

CONTROLLED RELEASE OF RADIONUCLIDES

CROSS-REFERENCE TO RELATED APPLICATIONS

The present application claims the benefit of U.S. Provisional Application 62/651,274, entitled "Controlled release of radium isotopes in the framework of DaRT (Diffusing alpha-emitters Radiation Therapy)", filed on Apr. 2, 2018, whose disclosure is incorporated herein by reference in its entirety.

FIELD OF THE INVENTION

The present invention relates generally to radiotherapy and particularly to methods of alpha brachytherapy.

BACKGROUND

Radiation is used to kill cancerous or other malignant cells. Different methods are known for delivery of the radiation to the cancerous cells. One of these methods involves use of radioactive atoms, which emit radiation. Most methods involving use of radioactive atoms use atoms which emit beta and gamma radiation, which have a relatively long range and therefore is easier to deliver target cancerous tissue. Alpha radiation, however, has much higher energy and therefore can be more effective in killing cancerous cells. The effective range of alpha radiation, however, is very short, and therefore to be effective the radioactive atoms which emit the alpha particles must be positioned very close to the malignant cells.

One method used to deliver alpha emitting radioactive atoms to malignant cells is targeted radionuclide therapy. In targeted therapy, carriers, such as liposomes, are connected to radioactive atoms and injected into the blood stream of a patient. During circulation, the liposomes attach to malignant cells and when alpha particles are emitted by the radioactive atoms at least some of the emitted alpha particles destroy the malignant cells.

PCT publication WO01/60417 to Larsen, titled "Radioactive Therapeutic Liposomes", PCT publication WO 02/05859 to Larsen, titled: "Method of Radiotherapy" and US patent publication 2004/0208821 to Larsen, titled: "Method of Radiotherapy", the disclosures of which are incorporated herein by reference in their entirety, describe liposomes which encapsulate heavy radionuclides which emit alpha particles. The radionuclides may include, among others, Radium-223, Radium-224 and Thorium-227. Daughter radionuclides generally remain trapped during nuclear transformation of the radionuclides.

Another method of delivering alpha radiation to malignant tissue is Brachytherapy, in which one or more seeds carrying a radioactive substance, also referred to as a radionuclide, are implanted in a tumor.

U.S. Pat. No. 8,834,837 and US patent publication 2009/0136422, which are incorporated herein by reference in their entirety, describe the use of a brachytherapy device with alpha radiation. The radioactive substance emits not only alpha radiation, but also daughter nuclei of the radioactive substance, which emit further alpha particles in a chain reaction. This increases the range of cells affected by the alpha radiation.

Various radionuclides have been suggested for use for brachytherapy.

US patent publication 2004/0242953 to Good, the disclosure of which is incorporated herein by reference, describes various isotopes which can be used for brachytherapy, including Thorium-228.

US patent publication 2013/0253255 to Van Niekerk, the disclosure of which is incorporated herein by reference, describes a brachytherapy seed carrying two disparate isotopes of the same substance.

US patent publication 2008/0249398 to Harder et al., the disclosure of which is incorporated herein by reference, describes a hybrid multi-radionuclide sealed source for use in brachytherapy.

It is generally desired to prevent the radionuclide from being washed away from the source by body fluids before the radionuclide has a chance to decay. PCT publication WO2018/207105, titled: "Polymer Coatings for Brachytherapy Devices", which is incorporated herein by reference in its entirety, describes coatings which are chosen to prevent the radionuclide from being washed, while not inhibiting the desorption of daughter nuclei from the source.

US patent publication 2002/0055667 to Mavity et al., the disclosure of which is incorporated herein by reference in its entirety, describes radionuclides with bio-absorbable structures that have a predefined persistence period which is usually substantially greater than the half-life of the radionuclides. The radionuclides remain localized and sequestered at a desired target site while significant radioactivity remains.

U.S. Pat. No. 8,821,364 to Fisher et al., the disclosure of which is incorporated herein by reference in its entirety, describes a brachytherapy seed made up of microspheres containing an alpha-particle-emitting radiation source and a resorbable polymer matrix, which rapidly dissolves.

SUMMARY

An aspect of some embodiments of the present invention relates to a brachytherapy device, comprising a base adapted for being at least partially introduced into a body of a subject and a plurality of radionuclide atoms of a first alpha-emitting isotope, coupled to the base in a manner that not more than 25% of the radionuclide atoms leave the base in 24 hours, in methods other than radioactive decay. When installed in a human subject, the brachytherapy device emits radionuclide atoms of the first alpha-emitting isotope at a rate of at least 0.1% of the number of radionuclide atoms of the first alpha-emitting isotope coupled to the base, per 24 hours.

Optionally, the first alpha-emitting isotope comprises Radium-224 and/or Radium-223. Optionally, the brachytherapy device includes a semi-porous polymer coating layer on the radionuclide atoms, configured to allow diffusion of a percentage of the radionuclide atoms, so as to provide the emission of the at least 0.1% of the number of radionuclide atoms of the first alpha-emitting isotope coupled to the base, per 24 hours. Optionally, the semi-porous polymer coating layer comprises PDMS (polydimethylsiloxane). Optionally, the semi-porous polymer coating layer has a thickness of no more than 0.5 microns. Optionally, the semi-porous polymer coating layer allows diffusion of the radionuclide atoms out of the brachytherapy device at a rate of at least 0.5% in 24 hours.

In some embodiments, the brachytherapy device further includes a base polymer coating layer on the base, and the plurality of radionuclide atoms are attached to the base polymer coating layer and thus coupled to the base in a manner allowing the radionuclide atoms to detach and diffuse, without nuclear decay. Optionally, the base polymer coating layer is configured to prevent diffusion of the radionuclide atoms therethrough. Optionally, the base polymer coating layer comprises polycarbonate. Optionally, the base polymer coating layer has a thickness of at least 0.25 microns. Optionally, the brachytherapy device emits radionuclide atoms of the first alpha-emitting isotope at a rate of at least 3% of the number of radionuclide atoms of the first alpha-emitting isotope coupled to the base, per 24 hours. Optionally, not more than 15% of the radionuclide atoms leave the base in 24 hours, in methods other than radioactive decay.

In some embodiments, the plurality of radionuclide atoms are coupled to the base in a manner that not more than 8% of the radionuclide atoms leave the base in 24 hours, in methods other than radioactive decay. Optionally, the brachytherapy device further includes a bio-absorbable polymer coating layer on the base, wherein the radionuclide atoms are embedded in the bio-absorbable polymer coating layer, and wherein when installed in a subject, the bio-absorbable polymer coating layer dissolves in a manner causing emission from the device of the at least 0.1% of the number of radionuclide atoms of the first alpha-emitting isotope coupled to the base, per 24 hours. Optionally, the radionuclide atoms are distributed substantially evenly in a thickness of the bio-absorbable polymer coating layer. Optionally, the brachytherapy device includes a plurality of radionuclide atoms of a second alpha-emitting isotope, which decays into the first alpha-emitting isotope, which are coupled to the base in a manner that the radionuclide atoms do not leave the brachytherapy device, but upon nuclear decay, a daughter nuclei of the decaying radionuclide atom is emitted from the device. Optionally, the plurality of radionuclide atoms of the second alpha-emitting isotope have an activity level of less than 20%, less than 10% or even less than 5% of the activity level of the radionuclide atoms of the first alpha-emitting isotope included in the device. Optionally, the plurality of radionuclide atoms of the second alpha-emitting isotope have an activity level greater than 1% of the activity level of the radionuclide atoms of the first alpha-emitting isotope included in the device. Optionally, the plurality of radionuclide atoms of the first alpha-emitting isotope constitute at least 50% of the radionuclide atoms in the brachytherapy device. Alternatively or additionally, the plurality of radionuclide atoms of the first alpha-emitting isotope provide at least 50% of the activity of the radionuclide atoms in the brachytherapy device. Optionally, the plurality of radionuclide atoms of the first alpha-emitting isotope have a density of at least $5*10^{10}$ atoms per square centimeter of the base.

An aspect of some embodiments of the present invention relates to a brachytherapy device, comprising a seed base adapted for being at least partially introduced into a body of a subject, a first coating layer on the seed base, configured to prevent passage of Radium-224 or Radium-223 therethrough, particles of a Radium-224 or Radium-223 radionuclide placed on the first coating layer, and a second coating layer on the particles, configured to allow diffusion of at least 0.1% of the particles of Radium.

Optionally, the seed base comprises a tube defining an internal channel. Optionally, the first coating layer comprises polycarbonate. Optionally, the first coating layer has a thickness of at least 0.05 microns, at least 0.1 microns, or even at least 0.3 microns. Optionally, the first coating layer has a thickness of no more than 1 micron or even no more than 0.5 microns.

Optionally, the second coating layer comprises PDMS (polydimethylsiloxane). Optionally, the second coating layer has a thickness of no more than 0.5 microns or even no more than 0.3 microns. Optionally, the second coating layer has a thickness of at least 0.1 microns. Optionally, the device allows diffusion of the particles of Radium through the second coating layer at a rate of at least 0.5% in 24 hours or even at least 5% in 24 hours. Optionally, the device allows diffusion of the particles of Radium through the second coating layer at a rate of no more than 10% in 24 hours or even no more than 2% in 24 hours.

An aspect of some embodiments of the present invention relates to a brachytherapy device, comprising a probe adapted for being at least partially introduced into a body of a subject, particles of Radium-224 retainably embedded on or beneath a surface of the probe, in a manner ensuring that the particles remain in the probe while a therapeutic dose of decay chain nuclei and alpha particles of said particles is emitted outside the surface; and particles of Thorium-228 retainably embedded on or beneath a surface of the probe, in a manner ensuring that the particles remain in the probe while a therapeutic dose of decay chain nuclei and alpha particles of said particles is emitted outside the surface. An activity level of the Thorium-228 particles is lower than 50% of an activity level of the particles of Radium-224 in the device.

Optionally, the probe comprises a removable probe. Optionally, the removable probe comprises a needle, a tip of an endoscope, a tip of a laparoscope or a tip of an imaging device. Optionally, the probe comprises a tube defining an internal channel. Optionally, the brachytherapy device includes a protective coat, coating the probe and the Thorium-228 radionuclide, wherein a thickness and a material of said protective coat is selected so as not to prevent said emission of said decay chain nuclei and said alpha particles. Optionally, the probe comprises an inner elongated member and an outer tubular member having a mouth section configured for receiving said inner elongated member, said inner elongated member being movable within said outer tubular member and having a distal end and a proximal end, whereby said radionuclide is on or beneath a surface of said distal end. Optionally, the probe and particles of a Thorium-228 are not coated. Optionally, the probe comprises a brachytherapy seed.

An aspect of some embodiments of the present invention relates to a method of brachytherapy treatment, comprising determining at least one property of a malignant tumor in a patient, selecting a layout of one or more seeds loaded with radionuclide atoms of a first isotope which emits alpha radiation, to be implanted in the malignant tumor, responsively to the determined at least one property, selecting for each of the one or more seeds, a rate of release of the first isotope from the seed, not including the release of alpha particles and daughter nuclei and installing seeds having the selected rates of release in the malignant tumor according to the selected layout. Optionally, the first isotope comprises Radium-224. Optionally, determining the at least one property of the malignant tumor comprises determining a shape and/or size of the malignant tumor. Optionally, installing the seeds comprises installing seeds having at least two substantially different rates of release of the first isotope.

DETAILED DESCRIPTION OF EMBODIMENTS

An aspect of some embodiments of the invention relates to a brachytherapy implant which carries an alpha-emitting radionuclide. The radionuclide is mounted on the implant in a manner which allows a small percentage of the radionuclide atoms to leave the implant and diffuse into nearby tissue. Optionally, the rate of release of radionuclide atoms is less than 5%, less than 4%, less than 3% or even less than 2% every 24 hours. Optionally, the rate of release of radionuclide atoms is greater than 0.1%, greater than 0.5% or even greater than 1% every 24 hours. The controlled release of the radionuclides at the desired rate increases the energy of decay particles that reaches farther points of a tumor in which the brachytherapy implant is installed, without allowing too large an amount of radiation to leave the tumor into surrounding healthy tissue.

In some embodiments, the desired rate of atom desorption is achieved by coating the brachytherapy implant with a coating having a thickness and/or other properties selected to allow a desired rate of desorption.

In other embodiments, the desired rate of atom desorption is achieved by including a bio-absorbable material with radionuclide atoms embedded therein, in the brachytherapy implant. The bio-absorbable material degrades when the brachytherapy implant is within the patient, and due to the degradation, the radionuclides leave the implant.

An aspect of some embodiments of the invention relates to a brachytherapy implant which carries a plurality of different alpha-emitting radionuclides. In some embodiments, the radionuclides have a substantial probability of having their daughter nuclide leave the brachytherapy implant into the tumor upon nuclear decay. Optionally, the plurality of different radionuclides include a parent nuclide and a daughter nuclide, which results from radioactive decay of the parent. In some embodiments, the parent nuclide comprises Thorium-228 and the daughter nuclide comprises Radium-224. In other embodiments, the parent nuclide comprises Thorium-227 and the daughter nuclide comprises Radium-223.

Figure 1:
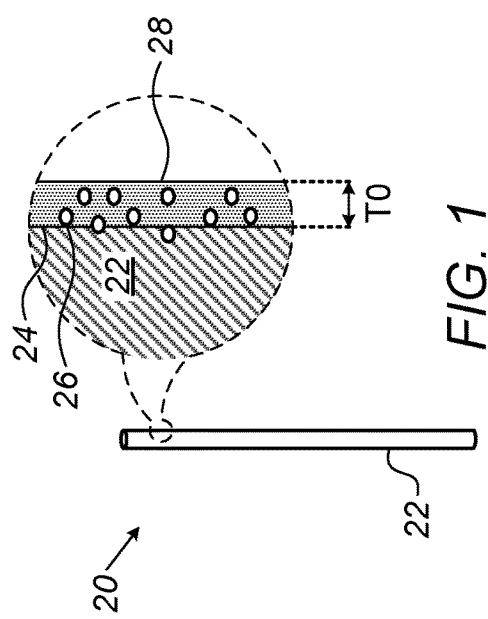
FIG. 1 is a schematic illustration of a brachytherapy device, in accordance with an embodiment of the present invention.

FIG. 1 is a schematic illustration of a brachytherapy device 20, in accordance with an embodiment of the present invention. Brachytherapy device 20 comprises a support 22, which serves as a base for device 20 and is configured for insertion into a body of a subject. Brachytherapy device 20 further comprises on an outer surface 24 of support 22, a bio-absorbable coating 28, having a thickness T0, with radionuclide atoms 26, dispersed therein throughout the thickness T0 of coating 28. It is noted that for ease of illustration, atoms 26 are drawn disproportionately large relative to the thickness of coating 28.

Support 22 comprises, in some embodiments, a seed for complete implant within a tumor of a patient, and may have any suitable shape, such as a rod or plate. In some embodiments, support 22 is cylindrically-shaped and has a diameter of 0.3-1 mm and/or a length of 5-60 mm. Alternatively to being fully implanted, support 22 is only partially implanted within a patient and is part of a needle, a wire, a tip of an endoscope, a tip of a laparoscope, or any other suitable probe.

Bio-absorbable coating 28 optionally comprises a semi-porous resorbable bio-compatible polymer matrix having a low resorption rate. The resorption rate is optionally lower than 1 micron, lower than 0.5 microns, lower than 0.2 microns or even lower than 0.1 microns a day. On the other hand, the resorption rate is not negligible and, in some embodiments, is higher than 0.05 microns, 0.1 microns, 0.3 microns or even higher than 0.8 microns a day. Optionally, the resorbable polymer matrix has a resorption rate of less than 20%, less than 10% or even less than 5% of the thickness of coating 28 per day. The resorption rate is optionally higher than 1%, 3%, 5% or even 10% per day. The resorption rate is optionally selected according to the half-life of the radionuclide atoms 26. In some embodiments, the resorption rate is such that at least 15%, 25% or even 40% of coating 28 dissolves within the half-life duration of radionuclide atoms 26 from the time at which brachytherapy device 20 is implanted. Optionally, the resorption rate is not too fast and less than 80%, less than 60%, less than 40% or even less than 25% of coating 28 dissolves within the half-life duration of radionuclide atoms 26 from the time at which brachytherapy device 20 is implanted.

Bio-absorbable coating 28 optionally comprises polylactide (PLA), polyglycolide (PGA) or co-polymers of PLA and PGA, tailored to achieve the desired resorption rate. Alternatively or additionally, coating 28 comprises co-poly lactic acid/glycolic acid (PLGA). The polymers of coating 28 optionally have molecular weights ranging from 5,000 to 100,000. The material of coating 28 dissolves in the patient through any of the methods known in the art, such as one or more of ultrasonic energy, reaction with body temperature and/or reaction with body fluids. Additional discussion of bio-absorbable polymers which may be used in accordance with embodiments of the present invention after adjustment for the desired resorption rate are described in above mentioned U.S. Pat. No. 8,821,364 and US patent publication 2002/0055667.

Bio-absorbable coating 28 typically has a thickness TO of between 0.5-10 microns, for example between 1-5 microns. Coating 28 is optionally thick enough to protect the radionuclide atoms 26 from being washed away before dissolution of coating 28, yet thin enough to allow the diffusion of the daughter radionuclides therethrough.

Radionuclide atoms 26 are optionally of an element which ejects alpha radiation in radioactive decay, and for which the daughter radionuclide easily diffuses through coating 28. The diffusion coefficient of the daughter radionuclide in the polymer may be at least $10^{-11}$ cm$^2$/sec. Preferably, the radionuclide atoms 26 are of an isotope which creates a chain of at least 3, or even at least 5 alpha emitting decay events until a stable or long half-life element is reached. Radionuclide atoms 26 optionally comprise an isotope of Radium (e.g., Ra-224 or Ra-223), which decays by alpha emission to produce a daughter isotope of Radon (e.g., Rn-220 or Rn-219), which decays by alpha emission to produce an isotope of Polonium (e.g., Po-216 or Po-215), which decays by alpha emission to produce an isotope of Lead (e.g., Pb-212 or Pb-211).

In some embodiments, all of radionuclide atoms 26 are of the same isotope. In other embodiments, radionuclide atoms 26 are of two or more different isotopes of the same element and/or of two or more different isotopes of different elements.

Typically, the density of radionuclide atoms 26 in coating 28 is between $10^{11}$ and $10^{14}$ atoms per square centimeter. The atoms 26 are optionally equally distributed throughout the thickness of coating 28.

Figure 2:
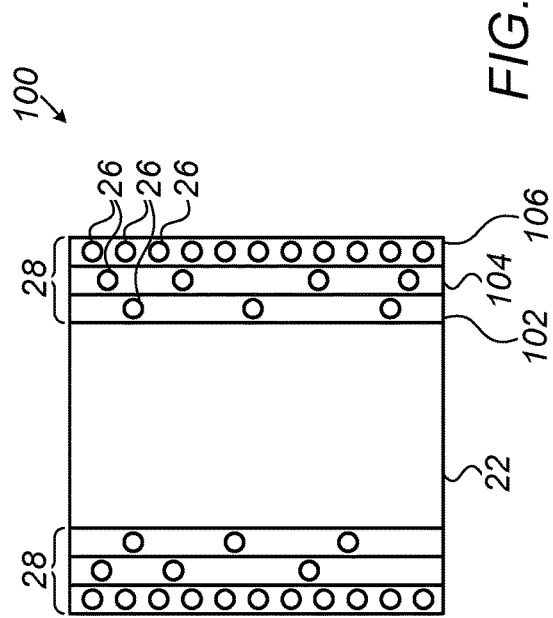
FIG. 2 is a schematic cross-section of a brachytherapy device, in accordance with another embodiment of the present invention.

FIG. 2 is a schematic illustration of a brachytherapy device 100, in accordance with an embodiment of the present invention. Brachytherapy device 100 is similar to device 20 of FIG. 1, but its bio-absorbable coating 28 is formed of a plurality of layers which differ in the composition of their polymer matrix and/or the concentration of radionuclide atoms 26 therein. As shown, coating 28 includes three layers which increase in their concentration of radionuclide atoms 26, as the layers are farther from support 22. A first layer 102, closest to support 22, has a first and lowest concentration of radionuclide atoms 26. A second layer 104 has a higher concentration than first layer 102, and a third layer 106, farthest from support 22 has a highest concentration of radionuclide atoms 26. Device 100 is presented by way of example, and in other embodiments, brachytherapy devices may have two layers or more than three layers. In addition, in other embodiments, the concentrations of radionuclide atoms 26 in the layers are different. Optionally, the concentration increases as the layers are closer to support 22. In some embodiments, the concentrations of the layers alternate between high and low levels and do not monotonously increase or decrease with the distance from support 22.

Alternatively or additionally to differing in concentration of radionuclide atoms 26, the layers of coating 28 differ in the resorption rate of their polymer structure. In one embodiment, the resorption rate is higher in outer layers than in inner layers. In other embodiments, the resorption rate is lower in outer layers than in inner layers.

Figure 3:
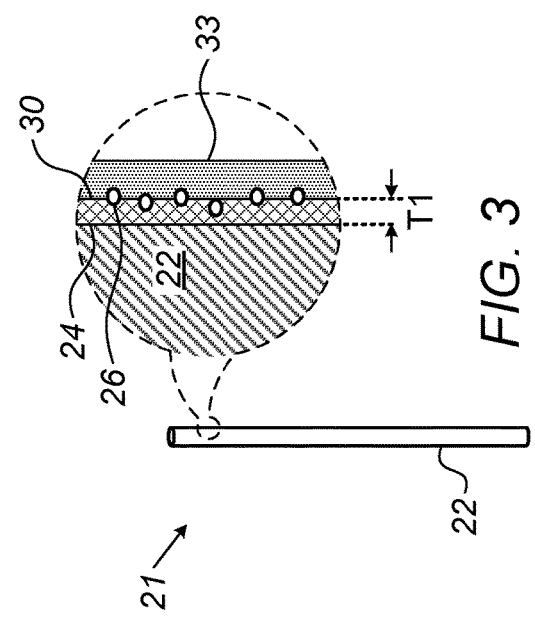
FIG. 3 is a schematic illustration of a brachytherapy device, in accordance with still another embodiment of the present invention.

FIG. 3 is a schematic illustration of a brachytherapy device 21, in accordance with another embodiment of the present invention. Device 21 differs from device 20 in that device 21 does not include a bio-absorbable coating, and instead has an outer layer 33 which allows slow diffusion of radionuclide atoms 26 out of device 20, at a desired rate. Optionally, device 21 includes two polymer layers: an inner layer 30 of a first polymer that coats outer surface 24, and outer layer 33 of a second polymer that coats inner layer 30. Atoms 26 are coupled to inner layer 30 and covered by outer layer 33 in a manner which generally keeps atoms 26 from leaving device 21, but allows slow diffusion of radionuclide atoms 26 out of device 20. On the other hand, outer layer 33 optionally allows daughter nuclides to easily leave device 21 as a result of nuclear decay and/or due to the properties of the daughter nuclei.

Outer layer 33 optionally comprises a biocompatible PDMS (polydimethylsiloxane) with a porosity and/or thickness adjusted to achieve the desired diffusion coefficient for radionuclide atoms 26. The thickness of layer 33 is optionally between 0.1 and 10 microns, for example between 0.1-0.3 microns, or between 0.5-1 microns. Layer 33 is optionally formed such that radionuclide atoms 26 have a diffusion coefficient therein of less than $10^{-13}$ cm$^2$/sec or even less than $2*10^{-14}$ cm$^2$/sec. Optionally, radionuclide atoms 26 have a diffusion coefficient in layer 33 greater than $2*10^{-15}$ cm$^2$/sec, possibly even greater than $8*10^{-15}$ cm$^2$/sec. On the other hand, the daughter nuclides of radionuclide atoms 26 optionally have a much higher diffusion coefficient in layer 33, for example, at least $10^{-11}$ cm$^2$/sec.

Inner layer 30 optionally comprises a material having a weaker bond to radionuclide atoms 26 than support 22, so as to allow atoms 26 to escape from device 21 without the energy of nuclear decay. In some embodiments, inner layer 30 comprises a polymer, such as polypropylene, polycarbonate (PC), polydimethylsiloxane, polyethylene terephthalate, poly(methyl methacrylate), and/or polysulfone, that coats surface 24. In some embodiments, inner layer 30 is also permeable to the daughter radionuclide; for example, the diffusion coefficient of the daughter radionuclide in layer 30 is at least $10^{-11}$ cm$^2$/sec. In other embodiments, inner layer 30 is less permeable to daughter nuclei, or even is substantially not permeable to daughter nuclei.

Typically, the thickness T1 of inner layer 30 is between 0.1 and 2 microns, such as between 0.1 and 1 microns. In some embodiments, inner layer 30 has a thickness of between about 0.2-0.4 microns, e.g., about 0.3 microns. In other embodiments, however, inner layer 30 is thinner than 0.1 microns, or even thinner than 50 nanometers. In still other embodiments, inner layer 30 is omitted and radionuclide atoms 26 are placed directly on support 22, and other means are used to prevent a strong bond between radionuclide atoms 26 and support 22. Typically, the density of radionuclide atoms 26 in device 21 is between $5*10^{10}$ and $10^{14}$ atoms per square centimeter.

The structure of layer 33 of device 21 and/or of coating 28 of device 20 are optionally selected so that at least 0.1%, at least 0.5% or even at least 1% of atoms 26 in the device leave the device through diffusion or dissolving of coating 28, per day. In some embodiments, the percentage of radionuclide atoms 26 that leave the device by diffusion or dissolving in a day is less than 3%, less than 2%, less than 1% or even less than 0.5%. Optionally, the number of atoms 26 that leave by diffusion or dissolving in a given time is less than 5%, less than 3%, less than 1% or even less than 0.5% of the number of atoms 26 that undergo nuclear decay in the given time. The number of atoms 26 that leave in methods other than nuclear decay is optionally greater than 0.1%, greater than 0.5% or even greater than 1% of the number of atoms 26 that undergo nuclear decay.

The diffusion or dissolving typically begins immediately or shortly after device 20 or 21 is installed in the patient, such that already in the first 24 hours after installation, or at most in the 48 hours after installation, at least 0.1% of radionuclide atoms 26 in the device leave the device through diffusion or dissolving.

Figure 4:
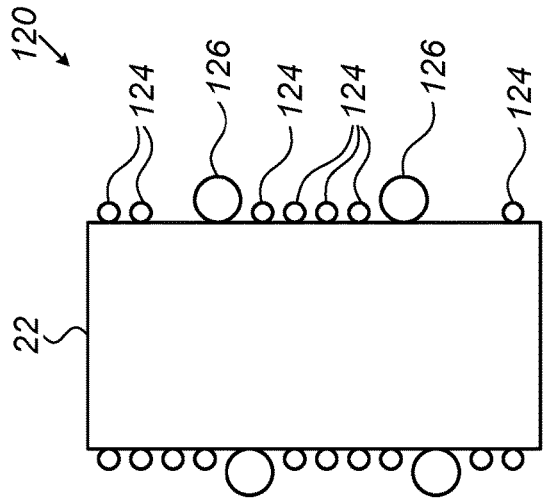
FIG. 4 is a schematic illustration of a brachytherapy device, in accordance with another embodiment of the present invention.

FIG. 4 is a schematic illustration of a brachytherapy device 120, in accordance with another embodiment of the present invention. Device 120 comprises a support 22 with radionuclide atoms 124 and 126 of two different elements on an outer surface 24 of support 22. Any suitable method known in the art may be used to attach radionuclide atoms 124 and 126 to support 22, such as thermal treatment as described, for example in US patent publication 2009/0136422, or a thin protective layer (not shown), such as a 5-10 nanometer layer of titanium.

Optionally, radionuclide atoms 124 are a daughter nuclide resulting from decay of radionuclide atoms 126. In some embodiments, radionuclide atoms 124 comprise Radium-224, while radionuclide atoms 126 comprise Thorium-228. Radionuclide atoms 126 optionally have an activity level of less than 50%, less than 20%, less than 10% or even less than 5% of the activity level of the radionuclide atoms of radionuclide atoms 124.

In an embodiment, radionuclide atoms 124 have an activity level of about 2 micro Ci, and radionuclide atoms 126 have an activity level of between about 40-100 nCi. The decay of Thorium-228 ejects a daughter radionuclide in the form of Radium-224, achieving an effect similar to that achieved by the devices of FIGS. 1-3.

The brachytherapy devices discussed above with reference to FIGS. 1-4, when based mainly on Radium-224 radionuclide atoms, allow a given percentage of the Radium-224 to leave the brachytherapy device without decay. Some of this Radium-224 will leave the tumor altogether, before it undergoes nuclear decay, as the half-life of Radium-224 is 3.66 days. Such lost Radium-224 atoms may not only be wasted, but also may reach and damage healthy tissue. Therefore, the prior art avoided release of radionuclide atoms having such a long half-life into the tumor. In accordance with the present invention, it has been determined that a release of a relatively small amount of Radium-224 into the tumor, is beneficiary and provides much needed energy to areas of the tumor distanced from the brachytherapy device. This benefit was determined to outweigh the drawback of lost radionuclide atoms.

In some embodiments of the invention, the percentage of Radium-224 radionuclide atoms allowed to leave the brachytherapy device is selected responsive to the size of the tumor. Optionally, seeds adjusted for release of different amounts of Radium-224 are provided to a physician and the physician selects a suitable seed responsive to the size of the tumor and the intended position in which the seed is to be implanted. Alternatively, the physician determines the size of the tumor and accordingly a suitable seed with a desired extent of release of Radium-224 is provided. In some embodiments, when implanting a plurality of seeds in a single tumor, different seeds may have different extents of release of Radium-224. For example, seeds implanted on the outskirts of the tumor optionally release small extents of Radium-224, or practically none, while seeds implanted in the center of the tumor release larger extents of Radium-224. In some embodiments, a physician determines a size and/or layout of a tumor and accordingly selects a number of seeds to be implanted in the tumor and/or the extent of release of Radium-224 of each of the seeds to be implanted.

In general, any suitable technique known in the art may be used to apply polymer coating 28 to device 20, or inner layer 30 and outer layer 33 to device 21, such as a dip-coating technique for example as described in above mentioned PCT publication WO2018/207105.

Typically, atoms 26 are generated by the decay of the preceding radionuclides in their decay chain. For example, as described in U.S. Pat. No. 8,894,969 to Kelson et al., atoms of Ra-224 may be generated by spreading a thin layer of acid containing Uranium-232 (U-232) on a metal. The U-232 decays to produce Thorium-228 (Th-228), which in turn decays to produce Ra-224.

Any suitable technique, such as any one or more of the techniques described in the aforementioned '969 patent to Kelson, may be used to couple atoms 26 to support 22. For example, a generating source that generates a flux of the radionuclide may be placed in a vacuum near support 22, such that nuclei recoiling from the generating source traverse the vacuum gap and are collected onto, or implanted in, surface 24. Alternatively, the radionuclide may be electrostatically collected onto support 22, by the application of a suitable negative voltage between the generating source and the support. In such embodiments, to facilitate the electrostatic collection of the radionuclide, support 22 may comprise an electrically-conductive metal, such as titanium. For example, support 22 may comprise an electrically-conducting metallic wire, needle, rod, or probe. Alternatively, support 22 may comprise a non-metallic needle, rod, or probe coated by an electrically-conductive metallic coating that comprises surface 24.

To treat a subject, at least one brachytherapy device is inserted fully or partially into the body of the subject, typically into, or immediately adjacent to (e.g., within 0.1 mm, such as within 0.05 mm or 0.001 mm, of) the tumor that is to be treated. Subsequently, while the brachytherapy device remains within the body, the radionuclide decays, thus emitting alpha particles, daughter nuclei and a percentage of the radionuclide atoms 26 into the tumor.

In some embodiments, following the radioactive decay of at least some of the radionuclide atoms, e.g., after a predetermined duration of time, and/or in response to monitoring the size of the tumor and/or the fraction of emitted alpha particles, the brachytherapy device is removed from the subject. In other embodiments, the device is not removed from the subject.

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

In some embodiments, combinations of the above described embodiments of FIGS. 1-4 are used. For example, a brachytherapy device may include a bio-absorbable layer for release of Radium embedded therein, and in addition include Thorium atoms attached to an inner support. As another example, a brachytherapy device may include a bio-absorbable and diffusible layer, which allows release of Radium or other radionuclide atoms through both diffusion and dissolving of the bio-absorbable layer.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. A brachytherapy device, comprising:
   a seed base adapted for being at least partially introduced into a body of a subject; and
   a plurality of radionuclide atoms of a first alpha-emitting isotope, coupled to the seed base, such that at least 0.1%, but not more than 25% of the plurality of radionuclide atoms coupled to the seed base leave the seed base in 24 hours, without radioactive decay,
   wherein daughter nuclei of the plurality of radionuclide atoms are released from the seed base upon radioactive decay.

2. The brachytherapy device of claim 1, wherein the first alpha-emitting isotope comprises Radium-224.

3. The brachytherapy device of claim 1, wherein the first alpha-emitting isotope comprises Radium-223.

4. The brachytherapy device of claim 1, further comprising a semi-porous polymer coating layer on the plurality of radionuclide atoms, configured to allow diffusion of a percentage of the plurality of radionuclide atoms, so that at least 0.1% of the plurality of radionuclide atoms of the first alpha-emitting isotope coupled to the seed base leave the seed base, per 24 hours.

5. The brachytherapy device of claim 4, wherein the semi-porous polymer coating layer comprises PDMS (polydimethylsiloxane).

6. The brachytherapy device of claim 4, wherein the semi-porous polymer coating layer has a thickness of no more than 0.5 microns.

7. The brachytherapy device of claim 4, wherein the semi-porous polymer coating layer allows diffusion of the plurality of radionuclide atoms out of the brachytherapy device at a rate of at least 0.5% in 24 hours.

8. The brachytherapy device of claim 4, further comprising a base polymer coating layer on the seed base, and wherein the plurality of radionuclide atoms are attached to the base polymer coating layer and thus coupled to the seed base in a manner allowing at least some of the plurality of radionuclide atoms to detach and diffuse, without nuclear decay.

9. The brachytherapy device of claim 8, wherein the base polymer coating layer is configured to prevent diffusion of the plurality of radionuclide atoms therethrough.

10. The brachytherapy device of claim 8, wherein the base polymer coating layer comprises polycarbonate.

11. The brachytherapy device of claim 8, wherein the base polymer coating layer has a thickness of at least 0.25 microns.

12. The brachytherapy device of claim 1, wherein the plurality of radionuclide atoms of the first alpha-emitting isotope are coupled to the seed base such that at least 3% of the plurality of radionuclide atoms of the first alpha-emitting isotope leave the seed base, per 24 hours.

13. The brachytherapy device of claim 1, wherein the plurality of radionuclide atoms of the first alpha-emitting isotope are coupled to the seed base such that not more than 15% of the plurality of radionuclide atoms leave the seed base in 24 hours.

14. The brachytherapy device of claim 1, wherein the plurality of radionuclide atoms of the first alpha-emitting isotope are coupled to the seed base such that not more than 8% of the plurality of radionuclide atoms leave the seed base in 24 hours.

15. The brachytherapy device of claim 1, further comprising a bio-absorbable polymer coating layer on the seed base, wherein the plurality of radionuclide atoms are embedded in the bio-absorbable polymer coating layer, and wherein when installed in the subject, the bio-absorbable polymer coating layer dissolves causing at least 0.1% of the plurality of radionuclide atoms of the first alpha-emitting isotope coupled to the seed base, to leave the seed base per 24 hours.

16. The brachytherapy device of claim 15, wherein the plurality of radionuclide atoms are distributed evenly in a thickness of the bio-absorbable polymer coating layer.

17. The brachytherapy device of claim 1, further comprising a plurality of radionuclide atoms of a second alpha-emitting isotope, which decays into the first alpha-emitting isotope, which are coupled to the seed base such that the plurality of radionuclide atoms of the second alpha-emitting isotope do not leave the brachytherapy device, but upon nuclear decay, a daughter radionuclide atom leaves the device.

18. The brachytherapy device of claim 17, wherein the plurality of radionuclide atoms of the second alpha-emitting isotope have an activity level of less than 20% of an activity level of the plurality of radionuclide atoms of the first alpha-emitting isotope included in the device.

19. The brachytherapy device of claim 18, wherein the plurality of radionuclide atoms of the second alpha-emitting isotope have an activity level of less than 10% of the activity level of the plurality of radionuclide atoms of the first alpha-emitting isotope included in the device.

20. The brachytherapy device of claim 18, wherein the plurality of radionuclide atoms of the second alpha-emitting isotope have an activity level of less than 5% of the activity level of the plurality of radionuclide atoms of the first alpha-emitting isotope included in the device.

21. The brachytherapy device of claim 17, wherein the plurality of radionuclide atoms of the second alpha-emitting isotope have an activity level greater than 1% of the activity level of the plurality of radionuclide atoms of the first alpha-emitting isotope included in the device.

22. The brachytherapy device of claim 1, wherein the plurality of radionuclide atoms of the first alpha-emitting isotope provide at least 50% of an activity of the brachytherapy device.

23. The brachytherapy device of claim 1, wherein the plurality of radionuclide atoms of the first alpha-emitting isotope have a density of at least $5*10^{10}$ atoms per square centimeter of the seed base.

24. A brachytherapy device, comprising:
    a seed base adapted for being at least partially introduced into a body of a subject;
    a first coating layer on the seed base, configured to prevent passage of Radium-224 or Radium-223 therethrough;
    particles of a Radium-224 or Radium-223 radionuclide placed on the first coating layer; and
    a second coating layer on the particles of the Radium-224 or Radium-223 radionuclide, configured to allow diffusion of at least 0.1% of the particles of the Radium-224 or Radium-223 radionuclide.

25. The brachytherapy device of claim 24, wherein the seed base comprises a tube defining an internal channel.

26. The brachytherapy device of claim 24, wherein the first coating layer comprises polycarbonate.

27. The brachytherapy device of claim 24, wherein the first coating layer has a thickness of at least 0.05 microns.

28. The brachytherapy device of claim 24, wherein the first coating layer has a thickness of at least 0.1 microns.

29. The brachytherapy device of claim 24, wherein the first coating layer has a thickness of at least 0.3 microns.

30. The brachytherapy device of claim 24, wherein the first coating layer has a thickness of no more than 1 micron.

31. The brachytherapy device of claim 24, wherein the first coating layer has a thickness of no more than 0.5 microns.

32. The brachytherapy device of claim 24, wherein the second coating layer comprises PDMS (polydimethylsiloxane).

33. The brachytherapy device of claim 24, wherein the second coating layer has a thickness of no more than 0.5 microns.

34. The brachytherapy device of claim 24, wherein the second coating layer has a thickness of no more than 0.3 microns.

35. The brachytherapy device of claim 24, wherein the second coating layer has a thickness of at least 0.1 microns.

36. The brachytherapy device of claim 24, wherein the device allows diffusion of the particles of the Radium-224 or Radium-223 radionuclide through the second coating layer at a rate of at least 0.5% in 24 hours.

37. The brachytherapy device of claim 24, wherein the device allows diffusion of the particles of the Radium-224 or Radium-223 radionuclide through the second coating layer at a rate of at least 5% in 24 hours.

38. The brachytherapy device of claim 24, wherein the device allows diffusion of the particles of the Radium-224 or Radium-223 radionuclide through the second coating layer at a rate of no more than 10% in 24 hours.

39. The brachytherapy device of claim 24, wherein the device allows diffusion of the particles of the Radium-224 or Radium-223 radionuclide through the second coating layer at a rate of no more than 2% in 24 hours.

40. A brachytherapy device, comprising:
a probe adapted for being at least partially introduced into a body of a subject;
particles of Radium-224 retainably embedded on or beneath a surface of the probe, in a manner ensuring that the particles of Radium-224 remain in the probe while a therapeutic dose of decay chain radionuclides and alpha particles of said particles of Radium-224 leaves the surface; and
particles of Thorium-228 retainably embedded on or beneath the surface of the probe, in a manner ensuring that the particles of Thorium-228 remain in the probe while a therapeutic dose of decay chain radionuclides and alpha particles of said particles of Thorium-228 leave the surface,
wherein an activity level of the particles of Thorium-228 is lower than 50% of an activity level of the particles of Radium-224 in the device.

41. The brachytherapy device of claim 40, wherein the probe comprises a removable probe.

42. The brachytherapy device of claim 41, wherein the removable probe comprises a needle, a tip of an endoscope, a tip of a laparoscope or a tip of an imaging device.

43. The brachytherapy device of claim 40, wherein the probe comprises a tube defining an internal channel.

44. The brachytherapy device of claim 40, further comprising a protective coat, coating the probe and the particles of Thorium-228, wherein a thickness and a material of said protective coat is selected so as not to prevent the decay chain radionuclides and the alpha particles from the particles of Thorium-228 from leaving the surface.

45. The brachytherapy device of claim 40, wherein the probe comprises an inner elongated member and an outer tubular member having a mouth section configured for receiving said inner elongated member, said inner elongated member being movable within said outer tubular member and having a distal end and a proximal end, whereby said particles of Radium-224 are on or beneath a surface of said distal end.

46. The brachytherapy device of claim 40, wherein the probe and particles of Thorium-228 are not coated.

47. The brachytherapy device of claim 40, wherein the probe comprises a brachytherapy seed.

48. The brachytherapy device of claim 1, wherein at least some of the plurality of radionuclide atoms that leave the seed base, leave a tumor in which the seed base is introduced, before undergoing nuclear decay.

49. The brachytherapy device of claim 1, wherein the seed base has a length of not less than 5 millimeters.

* * * * *